US011241891B2

(12) United States Patent
Luo et al.

(10) Patent No.: US 11,241,891 B2
(45) Date of Patent: Feb. 8, 2022

(54) ULTRASONIC DETECTION METHOD, ULTRASONIC DETECTION SYSTEM, AND RELATED APPARATUS

(71) Applicant: CLOUDMINDS (SHENZHEN) HOLDINGS CO., LTD., Guangdong (CN)

(72) Inventors: Lei Luo, Guangdong (CN); Qingwei Ji, Guangdong (CN)

(73) Assignee: CLOUDMINDS (SHENZHEN) HOLDINGS CO., LTD., Shenzhen (CN)

(*) Notice: Subject to any disclaimer, the term of this patent is extended or adjusted under 35 U.S.C. 154(b) by 167 days.

(21) Appl. No.: 16/569,829

(22) Filed: Sep. 13, 2019

(65) Prior Publication Data

US 2020/0085529 A1     Mar. 19, 2020

(30) Foreign Application Priority Data

Sep. 13, 2018 (CN) .......................... 201811068600.6

(51) Int. Cl.
*A61B 8/00* (2006.01)
*B41J 3/44* (2006.01)
(Continued)

(52) U.S. Cl.
CPC ............ *B41J 3/445* (2013.01); *A61B 8/14* (2013.01); *A61B 90/39* (2016.02); *B41J 3/4073* (2013.01);
(Continued)

(58) Field of Classification Search
CPC ......... B41J 3/445; B41J 3/4073; A61B 90/39; A61B 8/14; A61B 2090/065;
(Continued)

(56) References Cited

U.S. PATENT DOCUMENTS 10,034,658 B2 * 7/2018 Raju .................... A61B 5/6842
2005/0113691 A1   5/2005 Liebschner
(Continued)

FOREIGN PATENT DOCUMENTS

CN      201070878 Y      6/2008
CN      201168052 Y      12/2008
(Continued)

OTHER PUBLICATIONS

Office Action for Japanese Patent Application No. 2019-166532 dated Sep. 14, 2020.
(Continued)

*Primary Examiner* — Joel Lamprecht
(74) *Attorney, Agent, or Firm* — Heslin Rothenberg Farley & Mesiti P.C.

(57) ABSTRACT

Some embodiments of the present disclosure relate to the technical field of ultrasonic detection, and disclose an ultrasonic detection method, an ultrasonic detection system, and a related apparatus. The ultrasonic detection method includes: acquiring a reflected ultrasonic signal transmitted by an ultrasonic detector; generating an ultrasonic image in accordance with the reflected ultrasonic signal and displaying the ultrasonic image; acquiring information of a mark input by an operator based on the ultrasonic image; determining print information in accordance with the information of the mark; and transmitting the print information to the ultrasonic detector, causing the ultrasonic detector to add the mark on a surface of detected object in accordance with the print information. In the present disclosure, a target position of the detected object may be marked in the ultrasonic detection process.

18 Claims, 6 Drawing Sheets

(51) Int. Cl.
    *A61B 90/00* (2016.01)
    *A61B 8/14* (2006.01)
    *B41J 3/407* (2006.01)
    *G01L 5/00* (2006.01)
    *G01N 29/04* (2006.01)
    *G01N 29/22* (2006.01)
    *A61B 8/08* (2006.01)

(52) U.S. Cl.
    CPC .............. *G01L 5/00* (2013.01); *G01N 29/048* (2013.01); *G01N 29/22* (2013.01); *A61B 8/461* (2013.01); *A61B 8/5207* (2013.01); *A61B 2090/065* (2016.02); *A61B 2090/395* (2016.02)

(58) Field of Classification Search
    CPC . A61B 2090/395; A61B 8/461; A61B 8/5207; A61B 8/4427; A61B 8/469; G01L 5/00; G01N 29/048; G01N 29/22; G01N 29/0654; G01N 29/043; G01N 29/265; G01N 29/04
    See application file for complete search history.

(56) References Cited

U.S. PATENT DOCUMENTS

2006/0004290 A1* 1/2006 Smith .................. G01S 15/899
    600/459
2017/0334195 A1 11/2017 Brassil et al.

FOREIGN PATENT DOCUMENTS

| | | | |
|---|---|---|---|
| CN | 101368974 | A | 2/2009 |
| CN | 101391538 | A | 3/2009 |
| CN | 201341897 | Y | 11/2009 |
| CN | 101813638 | A | 8/2010 |
| CN | 103192610 | A | 7/2013 |
| CN | 103760236 | A | 4/2014 |
| CN | 105467005 | A | 4/2016 |
| CN | 105527343 | A | 4/2016 |
| CN | 107132275 | A | 9/2017 |
| JP | S56162044 | A | 12/1981 |
| JP | S6254710 | U | 4/1987 |
| JP | H01259973 | A | 10/1989 |
| JP | 2001259973 | A | 9/2001 |
| JP | 2016-508813 | A | 3/2016 |
| JP | 2016057187 | A | 4/2016 |
| JP | 2017213348 | A | 12/2017 |

OTHER PUBLICATIONS

Office Action for Chinese Patent Application No. 201811068600.6 dated Jul. 20, 2020.
Office Action for Chinese Patent Application No. 201811068600.6 dated Mar. 30, 2021.
Office Action for Japanese Patent Application No. 2019-166532 dated May 27, 2021.
Cloudminds (Shenzhen) Holdings Co., Ltd., CN First Office Action with English translation, CN201811068600.6, dated Jul. 20, 2020, 15 pgs.

* cited by examiner

ULTRASONIC DETECTION METHOD, ULTRASONIC DETECTION SYSTEM, AND RELATED APPARATUS

CROSS-REFERENCE TO RELATED DISCLOSURE

This application claims the priority benefit of Chinese Patent Application No. 201811068600.6 filed on Sep. 13, 2018 and entitled "ULTRASONIC DETECTION METHOD, ULTRASONIC DETECTION SYSTEM, AND RELATED APPARATUS", the disclosure of which is incorporated by reference herein in its entirety.

TECHNICAL FIELD

The present disclosure relates to the field of ultrasonic detection technologies, and in particular, to an ultrasonic detection method, an ultrasonic detection system, and a related apparatus.

BACKGROUND

Most of current ultrasonic detection devices are bulky professional equipment. There are a few ultrasonic detection devices whose sizes are relatively small and that may be held by hand to perform detection. However, an ultrasonic detection device as such has a structure in which a hand-held end is separated from a processing end, and a screen display is generally disposed at the processing end. In other words, when a hand-held ultrasonic detection device is being used to perform detection, one hand is required to hold the processing end with a screen, and the other hand is required to hold an ultrasonic hand-held end to perform detection.

In the process of studying the existing technology, inventors find that when using the hand-held ultrasonic detection device to perform detection, both hands are needed at the same time. For an ordinary ultrasonic detection, this method is feasible, but no free hand is available if an additional operation is required during the ultrasonic detection. For example, when an operation such as infusion needling or carotid puncture is required during the ultrasonic detection in accordance with an ultrasonic display, even if the processing end and the display end are put aside to release one hand, it is very difficult to carry out the operation because both a needling position and a current blood vessel's position on the screen need to be watched. A success rate is still relatively low, though higher than that in a case without ultrasonic assistance.

SUMMARY

A technical problem to be solved in some embodiments of the present disclosure is to provide an ultrasonic detection method, an ultrasonic detection system, and a related apparatus, so that a target position of a detected object may be marked during a ultrasonic detection process.

One embodiment of the present disclosure provides an ultrasonic detector, a print head is disposed at a detection surface of the ultrasonic detector;

The print head is configured to add a mark on a surface of a detected object that contacts the detection surface.

One embodiment of the present disclosure further provides an ultrasonic detection method applied to an ultrasonic imager, the ultrasonic detection method including:

acquiring a reflected ultrasonic signal transmitted by an ultrasonic detector;

generating an ultrasonic image in accordance with the reflected ultrasonic signal and displaying the ultrasonic image;

acquiring information of a mark input by an operator based on the ultrasonic image;

determining print information in accordance with the information of the mark; and transmitting the print information to the ultrasonic detector for adding a mark on a surface of a detected object in accordance with the print information.

An embodiment of the present disclosure further provides an ultrasonic detection apparatus, including: a first acquiring module, a display module, a second acquiring module, a determining module, and a transmitting module.

The first acquiring module is configured to acquire a reflected ultrasonic signal transmitted by an ultrasonic detector.

The display module is configured to generate an ultrasonic image in accordance with the reflected ultrasonic signal and display the ultrasonic image.

The second acquiring module is configured to acquire information of a mark input by an operator based on the ultrasonic image;

The determining module is configured to determine the print information in accordance with the information of the mark.

The transmitting module is configured to transmit the print information to the ultrasonic detector for adding the mark on a surface of a detected object in accordance with the print information.

An embodiment of the present disclosure further provides an ultrasonic imager, including:

at least one processor; and a memory in communication connection with the at least one processor.

Herein, the memory stores an instruction executable by the at least one processor, the instruction executed by the at least one processor, causing the at least one processor to be able to perform the forgoing ultrasonic detection method.

An embodiment of the present disclosure further provides a computer readable storage medium that stores a computer program. The computer program, when executed by a processor, implements the foregoing ultrasonic detection method.

An embodiment of the present disclosure further provides an ultrasonic detection system, including the foregoing ultrasonic detector and the forgoing ultrasonic imager.

Compared with the existing art, in embodiments of the present disclosure, the ultrasonic imager may acquire the information of the mark input by the operator and transmit the information of the mark to the ultrasonic detector which is provided with a print head causing the information of the mark to be printed on the surface of the detected object, thereby facilitating the operator performing another operation on the detected object in accordance with the mark, and preventing a case, in which it is impossible to determine an accurate operating position in accordance with a displayed image while viewing the ultrasonic displayed image during detection using an ultrasonic detection system, and thereby increasing a success rate of operation by the operator and improving user experience because the accurate operation position may be determined in accordance with the mark.

In addition, the ultrasonic detector further includes a pressure sensor and a processor. The pressure sensor is disposed at the detection surface. The pressure sensor is configured to acquire a value of a pressure between the detection surface and the detected object and transmit a pressure value to the processor, and the processor is configured to control the print head to add a mark on the surface of the detected object in accordance with the acquired pressure value.

The ultrasonic detector may determine a pressure between the ultrasonic detector and the detected object in accordance with the pressure value of the pressure sensor and determine to add a mark in accordance with the pressure value, so that the mark may be accurately printed on the surface of the detected object.

In addition, the print head includes a nozzle and an ink chamber, the ink chamber is filled with ink, the ink chamber is connected with the nozzle, and the nozzle is disposed at the detection surface. The processor is specifically configured to control the ink in the ink chamber to be ejected from the nozzle in accordance with the pressure value.

The pressure value is used to control whether the ink is ejected, further improving accuracy of mark printing.

Further, the print head includes at least two print units.

Further, the at least two print units are evenly distributed at the detecting surface.

The even distribution of the print units may ensure that anywhere on the detection surface may be marked, making the position of the mark printing more accurate.

Further, the processor is specifically configured to determine the pattern of the mark and adding position information, and control the print head to add a mark on the surface of the detected object in accordance with the pattern of the mark and the adding position information in accordance with the acquired pressure value.

Further, the information of the mark includes a pattern of the mark and display position of the mark. The determining the print information in accordance with the information of the mark includes: determining a pixel position of the mark on the ultrasonic image in accordance with the pattern of the information and the display position of the mark; determining a position of the print head corresponding to the pixel position of the mark on the ultrasonic image in accordance with a corresponding relation between the pixel position of the ultrasonic image and the position of the print head; and causing the determined position of the print head to be taken as the print information.

Further, the information of the mark includes a pattern of the mark and a display position of the mark. The determining the print information in accordance with the information of the mark includes: determining a pixel position of the mark on the ultrasonic image in accordance with the pattern of the information and the display position of the mark; and causing the pixel position of the mark on the ultrasonic image to be taken as the print information.

That an accurate printing position is determined in accordance with a pixel position on the ultrasonic image causes a printed mark position to be more accurate.

BRIEF DESCRIPTION OF THE DRAWINGS

One or more embodiments are exemplarily described through figures in accompanying drawings corresponding to the one or more embodiments. These exemplary descriptions do not constitute any limitation to the embodiments. Elements having identical reference numerals in the accompanying drawings are represented as similar elements. Unless otherwise stated, the figures in the accompanying drawings do not constitute any proportional limitation.

DETAILED DESCRIPTION

In order to make the purpose, the technical solutions and the advantages of the present disclosure clearer, some embodiments of the present disclosure will be explained below in detail with reference to the accompanying drawings and embodiments. It should be understood that the specific embodiments described here only explain the disclosure but do not impose a limitation to the disclosure. However, it will be apparent to those skilled in the art that, in the various embodiments of the present disclosure, numerous technical details are set forth in order to provide the reader with a better understanding of the present disclosure. However, the technical solutions claimed in the present disclosure may be implemented without these technical details and various changes and modifications based on the following embodiments.

Figure 1:
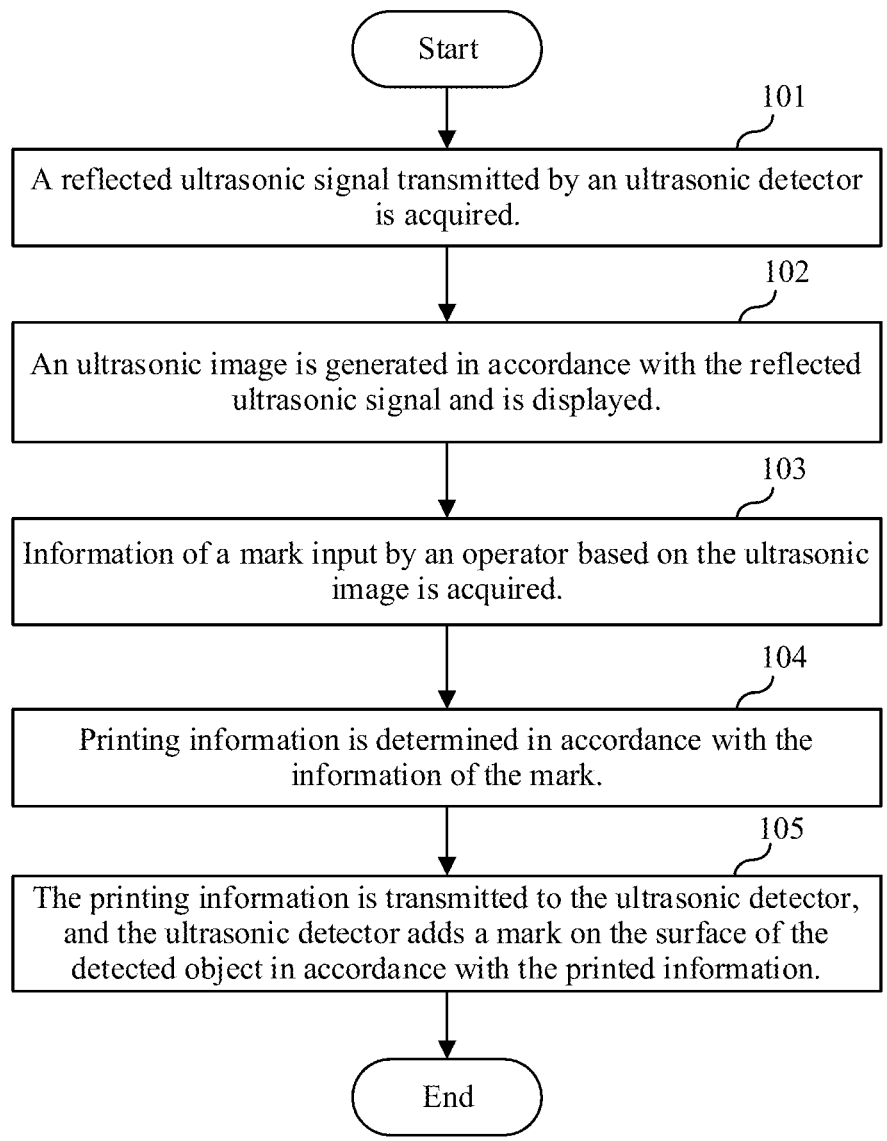
FIG. 1 is a flowchart of an ultrasonic detection method in accordance with a first embodiment of the present disclosure.

A first embodiment of the present disclosure relates to an ultrasonic detection method applied to an ultrasonic imager, and an implementation process of the ultrasonic detection method is shown in FIG. 1. The implementation process includes the following steps.

In step 101, a reflected ultrasonic signal transmitted by an ultrasonic detector is acquired.

In particular, the ultrasonic imager and the ultrasonic detector cooperate together to realize the ultrasonic detection method of this embodiment. The reflected ultrasonic signal is acquired by the ultrasonic detector and transmitted to the ultrasonic imager, and the ultrasonic imager performs imaging processing in accordance with the reflected ultrasonic signal acquired by the ultrasonic detector. Here, a type of the reflected ultrasonic signal acquired by the ultrasonic imager is not specifically limited, and the ultrasonic detector may directly transmit the acquired reflected ultrasonic signal to the ultrasonic imager, or may perform preprocessing on the acquired reflected ultrasonic signal and transmit the preprocessed reflected ultrasonic signal to the ultrasonic imager, which is not specifically limited herein.

In step 102, an ultrasonic image is generated in accordance with the reflected ultrasonic signal and is displayed.

In particular, a specific embodiment of generating the ultrasonic image in accordance with the reflected ultrasonic signal after processing is similar to a known imaging manner of the reflected ultrasonic signal, and details are not described herein again.

Here, if the ultrasonic imager acquires the reflected ultrasonic signal directly reflected to the ultrasonic detector, the ultrasonic imager performs imaging processing and displays the ultrasonic image after the imaging processing; if the ultrasonic imager acquires a preprocessed reflected ultrasonic signal, the ultrasonic imager generates the ultrasonic image in accordance with the preprocessed reflected ultrasonic signal and displays the ultrasonic image.

In step 103, information of a mark input by an operator based on the ultrasonic image is acquired.

In particular, the operator inputs the information of the mark to the ultrasonic imager based on an input device of the ultrasonic imager. Herein, the operator may view the ultrasonic image on a display screen and mark the ultrasonic image. If it is possible for the display screen of the ultrasonic imager to acquire the information of the mark input by the operator, e.g., the display screen is a touch screen, the operator may directly input the information of the mark on the display screen. For example, the operator may input the information of the mark on the touch screen with a finger or a stylus. If another input device such as a mouse or a keyboard is provided to the ultrasonic imager, the operator may input the information of the mark to the ultrasonic imager by dragging the mouse or inputting a control command using the keyboard. Therefore, a manner in which the operator inputs the information of the mark is not specifically limited in this embodiment.

In particular, the ultrasonic imager may process the acquired information of the mark in real time. For example, the acquired information of the mark is processed in real time and transmitted to a corresponding ultrasonic detector which performs marking in accordance with a real-time control command. Alternatively, the ultrasonic imager processes and outputs the information of the mark after determining the information of the mark input by the operator. For example, a user inputs the information of the mark on a screen and inputs the information of the mark to the ultrasonic imager with a hand or a stylus. While the operator is inputting the information of the mark on the touch screen, the ultrasonic imager is processing the information of the mark. Alternatively, after the user determines the input information of the mark, the user may determine, by acquiring a determining command input by the operator, information of the operator finishing marking, and process and output the information of the mark. A specific manner of processing the ultrasonic imager is not limited herein.

In step 104, print information is determined in accordance with the information of the mark.

It should be noted that the ultrasonic imager cooperates with the ultrasonic detector, and the print information needs to be transmitted to the ultrasonic detector which performs printing on a surface of a detected object in accordance with the print information.

In particular, when the operator inputs the information of the mark to the ultrasonic imager, the information of the mark includes a pattern of the mark input by the operator and a display position of the mark. Therefore, a specific implementation process of determining the print information in accordance with the information of the mark is as follows: determining a pixel position of the mark on the ultrasonic image in accordance with the pattern of the mark and the display position of the mark; determining a position of the print head corresponding to the pixel position marked on the ultrasonic image in accordance with a corresponding relation between the pixel position on the ultrasonic image and the position of the print head; and causing the determined position of the print head to be taken as the print information.

Here, a position of the information of the mark on the surface of the detected object may be accurately determined by determining the position of the print head corresponding to the pixel position marked on the ultrasonic image in accordance with the corresponding relation between the pixel position on the ultrasonic image and the position of the print head, thereby increasing a success rate of operation by an operator.

In step 105, the print information is transmitted to the ultrasonic detector, and the ultrasonic detector adds a mark on the surface of the detected object in accordance with the print information.

Data transmission between the ultrasonic detector and the ultrasonic imager may be wired data transmission or wireless data transmission. A manner of a specific connection and communication between the ultrasonic detector and the ultrasonic imager is not specifically limited herein.

It is worth mentioning that the foregoing ultrasonic detection method applied to the ultrasonic imager may be applied to an ultrasonic detection device for human body detection, or may be applied to an ultrasonic detection device for ultrasonic flaw detection in equipment detection, which is not specifically limited herein.

Compared with the existing technology, the ultrasonic imager may acquire the information of the mark input by the operator and transmit the information of the mark to the ultrasonic detector which is provided with a print head causing the information of the mark to be printed on the surface of the detected object, thereby facilitating the operator performing another operation on the detected object in accordance with the mark, and preventing a case in which it is impossible to determine an accurate operating position in accordance with a displayed image while viewing the ultrasonic displayed image during detection using an ultrasonic detection system, and thereby increasing a success rate of operation by the operator and improving user experience because the accurate operation position may be determined in accordance with the mark.

Figure 2:
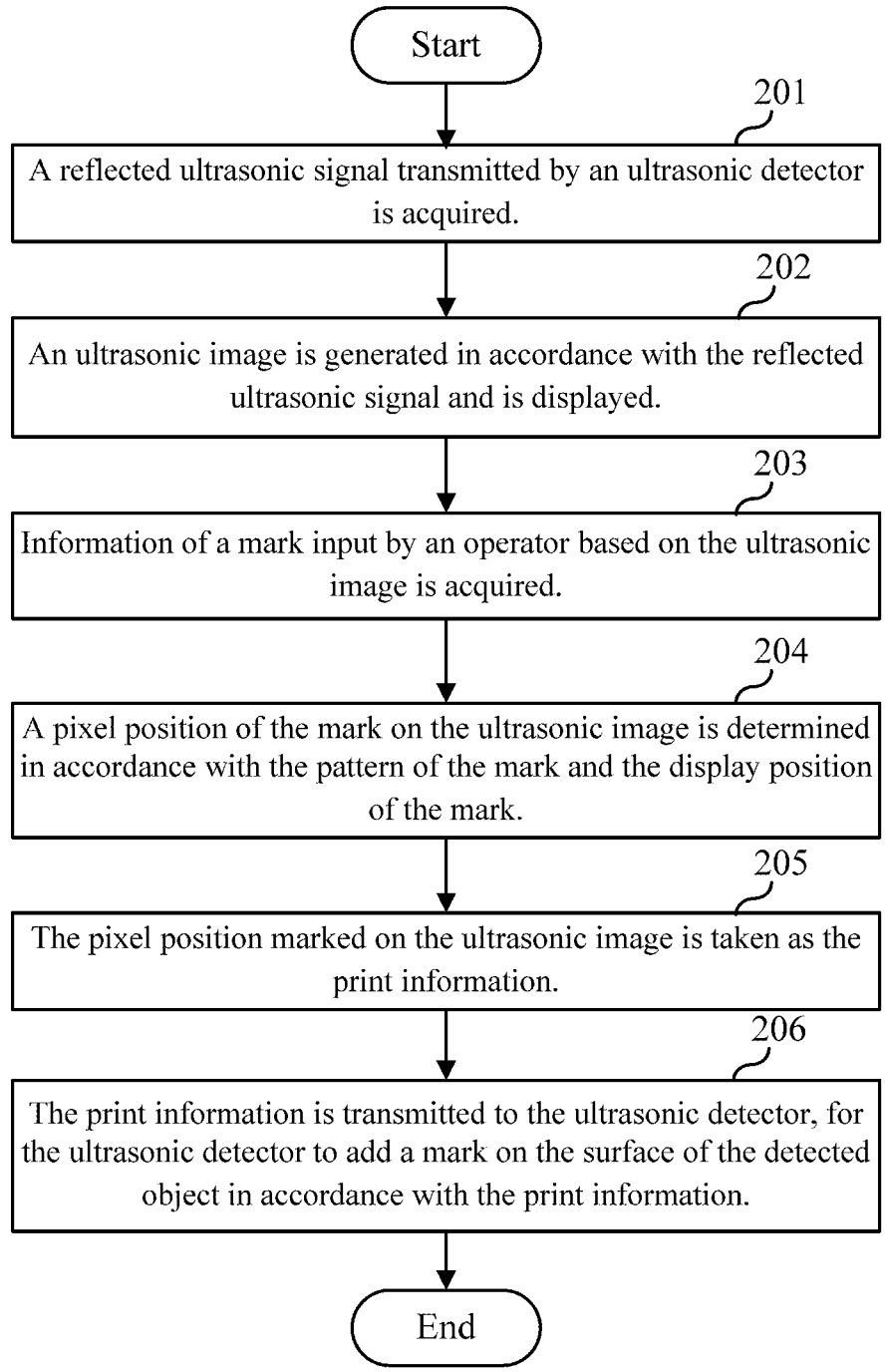
FIG. 2 is a flowchart of an ultrasonic detection method in accordance with a second embodiment of the present disclosure.

A second embodiment of the present disclosure discloses an ultrasonic detection method. The second embodiment is roughly the same as the first embodiment, and a main difference lies in that an implementation of determining the information of the mark is mainly described in the second embodiment. A specific process of the second embodiment is shown in FIG. 2. It should be noted that, in this embodiment, step 201 to step 206 are included. Step 201 to step 203 and 206 are the same as step 101 to step 103 and step 105 in the first embodiment respectively, and are not repeated, but only differences are described herein.

In step 204, a pixel position of the mark on the ultrasonic image is determined in accordance with the pattern of the mark and the display position of the mark.

It should be noted that, in this embodiment, the print information is directly determined in accordance with the pixel position marked on the ultrasonic image, but the position of the print head for performing mark printing does not need to be determined, and a processing speed of the ultrasonic imager is faster.

In particular, the pixel position determined in accordance with the information of the mark is referred to as an absolute position for printing the mark. The absolute position for printing the mark may avoid a problem that the position of the information of the mark changes due to a real-time change to a displayed ultrasonic image, so that the print information is more accurate.

In step 205, the pixel position marked on the ultrasonic image is taken as the print information.

Figure 3:
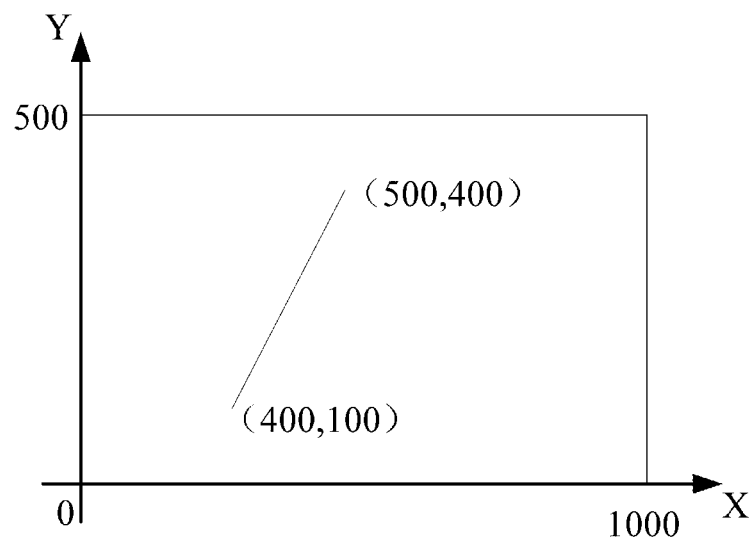
FIG. 3 is a schematic diagram of information of a mark on an ultrasonic imager in accordance with a second embodiment of the present disclosure.

In particular, a corresponding relation between the pixel position marked on the ultrasonic image and the print head depends on an actual size of an ultrasonic detector in practice. For example, assuming that real pixels of the ultrasonic image is 1000×500 and a size of an actual imaging element of a probe is 5×1 cm (cm), as shown in FIG. 3, the information of the mark input by the operator to the ultrasonic imager is a straight line, and a rectangular coordinate system is established with a lower left corner of the ultrasonic detector as a coordinate origin. The pixel position of the information of the mark on the ultrasonic image is (400,100) to (500,400), which corresponds with equal ratio to a physical position of the ultrasonic detector, that is, a contact surface of the ultrasonic detector on the detected object. Therefore, the print information may be determined as a straight line from a transverse position (2 cm, 0.2 cm) to (2.5 cm, 0.8 cm) in accordance with the corresponding relation between the pixel position and a detection surface. Here, the coordinate position in the print information is also marked with the lower left corner of the probe in contact with the detected object as the coordinate origin.

Here, the pattern of the mark may be a pattern of any shape, and may be printed multiple times in multiple positions. In this embodiment, the pixel position of the mark on the ultrasonic image is directly taken as the print information, and the real-time printing may further be realized. For example, when detecting a human body using the detection device, if a direction of a blood vessel is to be marked, it may not be completely marked at one position, but may be marked on an ultrasonic imager again after moving the detection probe, and may be printed on the skin in real time. In this implementation, the print information may be printed on the surface of the detected object while acquiring the information of the mark, preventing occurrence of a marking error caused by movement of the ultrasonic probe.

Arrangement of the steps of the foregoing various methods are merely for clear description. During implementation, some steps may be combined into one step, or some step may be divided into multiple steps, and the steps including a same logic relationship shall fall within the protection scope of the present disclosure. Insignificant modification added or an insignificant design introduced to an algorithm or a process without changing a core design of the algorithm and process shall fall within the protection scope of the present disclosure.

Figure 4:
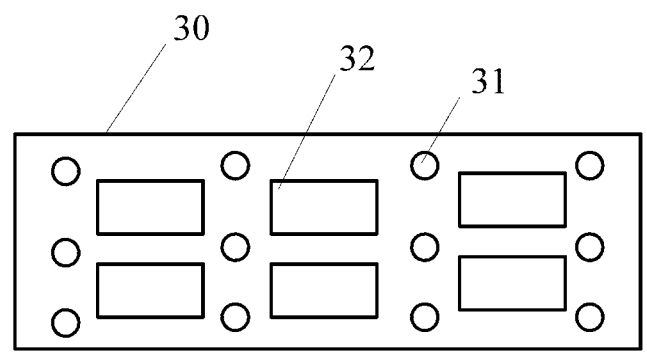
FIG. 4 is a structural diagram of an ultrasonic detector in accordance with a third embodiment of the present disclosure.

A third embodiment of the present disclosure discloses an ultrasonic detector, and a specific structure of the ultrasonic detector is shown in FIG. 4.

Here, print heads 31 are disposed at a detection surface 30 of the ultrasonic detector, and the print heads 31 are configured to add a mark on a surface of a detected object that contacts the detection surface 30.

It should be noted that the ultrasonic detector in this embodiment may be implemented in cooperation with the ultrasonic imager in the first or second embodiment, the technical details related to the ultrasonic detector in the first or second embodiment are still valid in this embodiment, relevant technical details in this embodiment are still valid in the first or second embodiment, and the relevant technical details are not repeated herein.

Here, the ultrasonic detector includes ultrasonic probes 32 configured to transmit ultrasonic signals and receive reflected ultrasonic signals, which is the same as an existing ultrasonic probe and will not be repeated herein.

In particular, in order to ensure that the print heads 31 accurately prints the print information on the surface of the detected object, the detection surface 30 of the ultrasonic detector is further provided with a pressure sensor for detecting whether an ultrasonic probe 32 is in contact with the detected object. The ultrasonic probe 32 is further provided with a processor. The pressure sensor acquires a pressure value between the detection surface 30 and the detected object and transmits the pressure value to the processor. The processor controls the print heads 31 to add a mark on the surface of the detected object in accordance with the acquired pressure value.

In particular, a preset pressure value may be set to determine whether the detection surface 30 is in contact with the detected object. Here, the preset pressure value may be 0. If the pressure value acquired by the pressure sensor is 0, it indicates that the detection surface 30 is not in contact with the detected object. If the pressure value acquired by the pressure sensor is not 0, it indicates that the detection surface 30 is in close contact with the detected object, and the print heads 31 print the mark on the surface of the detected object, thereby ensuring accuracy of the mark position. A specific setting of the preset pressure value is no limited herein.

In particular, a print unit of a print head 31 is configured to perform printing. Here, the ultrasonic detector instructs the print heads 31 to perform printing in accordance with a printing command transmitted by the ultrasonic imager. If the print information indicates a print unit of the ultrasonic detector that needs to enter a working state for this marking, the corresponding print unit enters the working state in accordance with the print information. If the print information includes a position to be marked and a pattern of the mark, but does not include the specific working print unit, the processor arranged in the ultrasonic detector is configured to determine the print unit that shall enter the working state. A specific implementation process is as follows: the processor determines the pattern of the mark and position information of the mark, determines the print unit entering the working state in accordance with the position information of the mark, controls the corresponding print unit to enter the working state in accordance with the acquired pressure value, and adds a mark on the surface of the detected object.

It should be noted that, it is not limited herein in a specific marking process whether the processor of the ultrasonic imager determines the specific working print unit or the processor of the ultrasonic detector determines the specific working print unit.

Here, the ultrasonic detector may mark the detected object in an ultrasonic detection process, but a specific application scenario of the ultrasonic detector is not limited. For example, in the ultrasonic detection process of a human body, if a position of a blood vessel is to be marked, the ultrasonic detector determines the print information in accordance with the information of the mark on the ultrasonic imager, and the ultrasonic detector adds a mark to the surface of the detected object in accordance with the print information. The operator may determine a position of the blood vessel in accordance with the position of the mark, facilitating the operator performing subsequent operations such as puncture or needling in accordance with the mark. For another example, in ultrasonic flaw detection on an equipment, if the equipment is to be marked on a position with a flaw, the equipment may be marked by the print heads 31 to facilitate subsequent processing on the equipment. It should be noted that application of the ultrasonic detector is not limited to the forgoing application scenarios, but is merely exemplified herein, and is not specifically limited.

Compared with the existing art, the ultrasonic detector in this embodiment may add a mark on the surface of the detected object, thereby facilitating the operator performing another operation on the detected object in accordance with the mark, and preventing a case, in which it is impossible to determine an accurate operating position in accordance with a displayed image while viewing the ultrasonic displayed image during detection using an ultrasonic detection system, and thereby increasing a success rate of operation by the operator and improving user experience because the accurate operation position may be determined in accordance with the mark.

A fourth embodiment of the present disclosure discloses an ultrasonic detector. The fourth embodiment is roughly the same as the third embodiment, and a main difference lies in that the specific arrangement of the print heads 31 is specifically described in the fourth embodiment of the present disclosure. Here, a print head includes at least two print units evenly distributed at the detection surface 30. The print heads 31 are distributed as shown in FIG. 5.

Here, at least two print units are evenly distributed at the detection surface, and the more the number of print units, the closer the printed mark is to the information of the mark. In addition, the print units may otherwise be unevenly distributed, and the distribution mode of the print units is not specifically limited herein.

Figure 5:
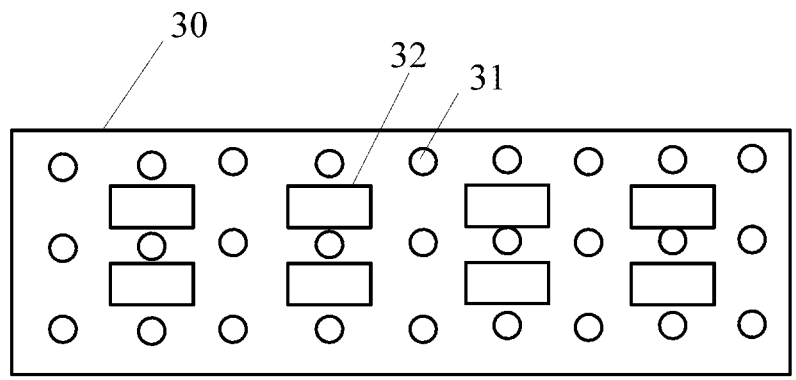
FIG. 5 is a structural diagram of an ultrasonic detector in accordance with a fourth embodiment of the present disclosure.

It should be noted that the distance between adjacent print units in FIG. 5 are equal. The print units are evenly distributed around an ultrasonic probe 32 configured to transmit an ultrasonic signal or receive a reflected ultrasonic signal. In order to ensure accuracy of printing, the print units are distributed as evenly as possible on the ultrasonic detecting surface 30. The larger the number of print units is set, the more the printing coordinate positions are on the detection surface 30, the more dots may be printed, the closer the printed image is to the pattern of the mark, and the higher the accuracy of the mark. The number and arrangement of the print units are not specifically limited herein.

In particular, in the process of marking by a print unit, the print unit ejects ink to perform marking at a corresponding position. A specific structure of the print unit is as follows: the print unit includes a nozzle and an ink chamber filled with ink. The ink chamber is connected to a nozzle disposed at the detection surface 30. Here, the processor controls operation of the print head 31 in accordance with the pressure value transmitted by the pressure sensor, that is, the processor controls the ink chamber to be squeezed to eject ink from the nozzle.

It should be noted that a particular structure of the print head 31 is not specifically limited, and herein printing performed by ejecting ink by squeezing the ink chamber is merely an example.

Here, components of the ink are harmless to a human body, thus the ultrasonic detector may be configured to detect and mark a human body. Besides, after being ejected, the ink may not be erased during movement of the ultrasonic probe, and may not affect accuracy of the mark.

Figure 6:
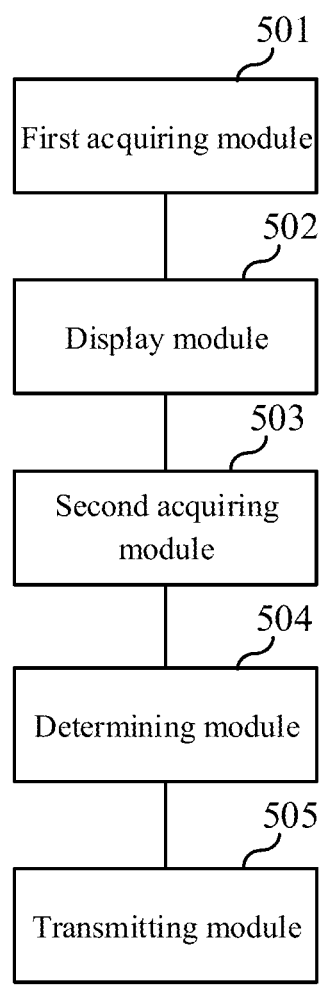
FIG. 6 is a schematic structural diagram of an ultrasonic detection apparatus in accordance with a fifth embodiment of the present disclosure.

As shown in FIG. 6, a fifth embodiment of the present disclosure discloses an ultrasonic detection apparatus, including: a first acquiring module 501, a display module 502, a second acquiring module 503, a determining module 504, and a transmitting module 505.

The first acquiring module 501 is configured to acquire a reflected ultrasonic signal transmitted by an ultrasonic detector.

The display module 502 is configured to generate an ultrasonic image in accordance with the reflected ultrasonic signal and display the ultrasonic image.

The second acquiring module 503 is configured to acquire information of a mark input by an operator based on the ultrasonic image.

The determining module 504 is configured to determine print information in accordance with the information of the mark.

The transmitting module 505 is configured to transmit the print information to the ultrasonic detector, for the ultrasonic detector to add the mark on a surface of a detected object in accordance with the print information.

It is not difficult to find that this embodiment is a system embodiment corresponding to the first embodiment, and this embodiment may be combined with the first embodiment for implementation. Related technical details mentioned in the first embodiment are still valid in this embodiment and are not described herein again to reduce repetition. Equivalently, related technical details mentioned in this embodiment may also be applied to the first embodiment.

It is worth mentioning that related various modules in this embodiment are all logic modules. In actual application, a logic unit maybe either a physical unit, or a part of a physical unit, or may be implemented through combination of a plurality of physical units. In addition, in order to highlight a creative portion of the present disclosure, a unit not closely related to solve the technical problems mentioned in the present disclosure is not introduced in this embodiment, which, however, does not mean that there are no other units in this embodiment.

Figure 7:
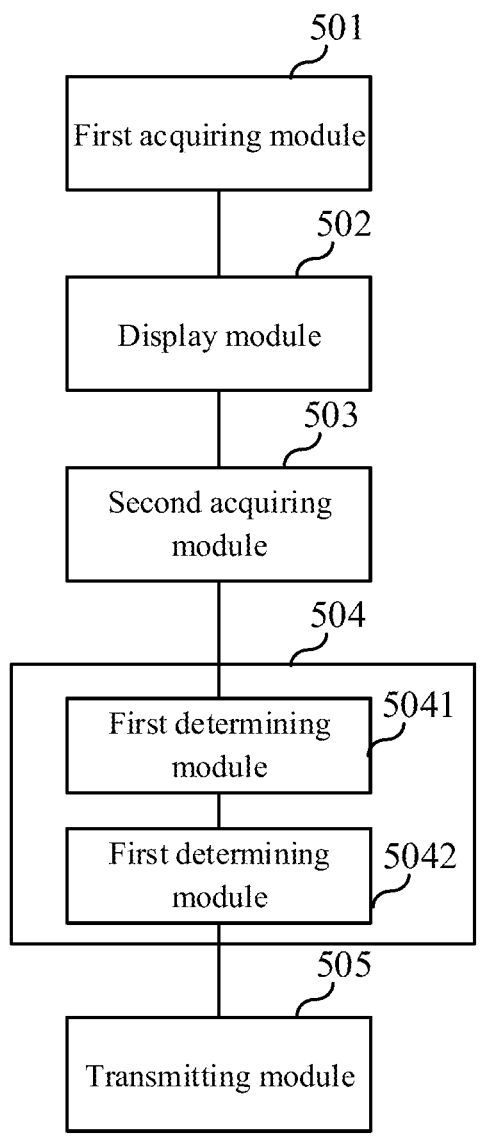
FIG. 7 is a schematic structural diagram of an ultrasonic detection apparatus in accordance with a sixth embodiment of the present disclosure.

A sixth embodiment of the present disclosure relates to an ultrasonic detection apparatus. The sixth embodiment is roughly the same as the fifth embodiment, and a main difference lies in that a specific function of the determining module 504 is specifically explained in the sixth embodiment. Herein, the determining module 504 includes a first determining sub-module 5041 and a second determining sub-module 5042, as shown in FIG. 7.

The first determining sub-module 5041 is configured to determine a pixel position of the mark on an ultrasonic image in accordance with a pattern of the mark and a display position of the mark.

The second determining sub-module 5042 is configured to use the pixel position marked on the ultrasonic image as the print information.

Since the second embodiment is corresponding to this embodiment, this embodiment may be combined with the second embodiment for implementation. Related technical details mentioned in the second embodiment are still valid in this embodiment, and a technical effect achieved in the second embodiment may also be achieved in this embodiment, which is not described herein again to reduce repetition. Equivalently, related technical details mentioned in this embodiment may also be applied to the second embodiment.

Figure 8:
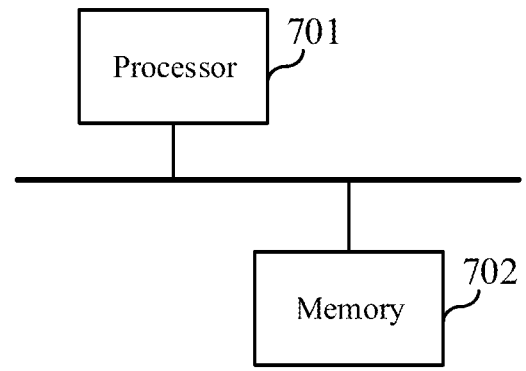
FIG. 8 is a schematic structural diagram of an ultrasonic imager in accordance with a seventh embodiment of the present disclosure.

A seventh embodiment of the present disclosure relates to an ultrasonic imager. As shown in FIG. 8, the ultrasonic imager includes at least one processor 701 and a memory 702 in communication with the at least one processor 701. Herein, the memory 702 stores an instruction executable by the at least one processor 701, and the instruction is executed by the at least one processor 701 to cause the at least one processor 701 to implement the ultrasonic detection method.

In this embodiment, that the processor 701 is a central processing unit (CPU) is used as an example, and that the memory 702 is a random-access memory (RAM) is used as an example. The processor 701 and the memory 702 may be connected through a bus or in other manners. In FIG. 8, that the processor 701 and the memory 702 are connected through a bus is used as an example. The memory 702, as a non-volatile computer readable storage medium, may be configured to store a non-volatile software program, a non-volatile computer-executable program and a module. For example, a program that implements the ultrasonic detection method in the embodiments of the present disclosure is stored in the memory 702. The processor 701 runs the non-volatile software program, instruction, and module stored in the memory 702 to implement various functional application programs of a device and data processing, that is, to realize the foregoing ultrasonic detection method.

The memory 702 may include a program storage area and a data storage area. Herein, the program storage area may store an operating system and an application program required for at least one function, and the data storage area may store an option list and the like. In addition, the memory may include a high-speed random-access memory, and may further include a non-volatile memory, such as at least one magnetic disk memory device, a flash memory device, or other non-volatile solid-state memory devices. In some embodiments, the memory 702 may alternatively include remotely disposed memories relative to the processor 701, and these remote memories may be connected to an external device via a network. Examples of the foregoing network includes, but is not limited to, the Internet, an intranet, a local area network, a mobile communication network, and a combination thereof.

One or more program modules are stored in the memory 702. When executed by one or more processors 701, the one or more program modules implement the ultrasonic detection method in the foregoing first method embodiment or second method embodiment.

The foregoing products may implement the ultrasonic detection method provided in the embodiments of the present disclosure, and have equivalent functional modules to implement the method and beneficial effects. For technical details not described in detail in this embodiment, the ultrasonic detection method provided in the embodiments of the present disclosure may be referred to.

An eighth embodiment of the present disclosure relates to a computer readable storage medium and a computer instruction is stored in the computer readable storage medium. The computer instruction causes a computer to implement the ultrasonic detection method in the first method embodiment or the second method embodiment of the present disclosure.

Figure 9:
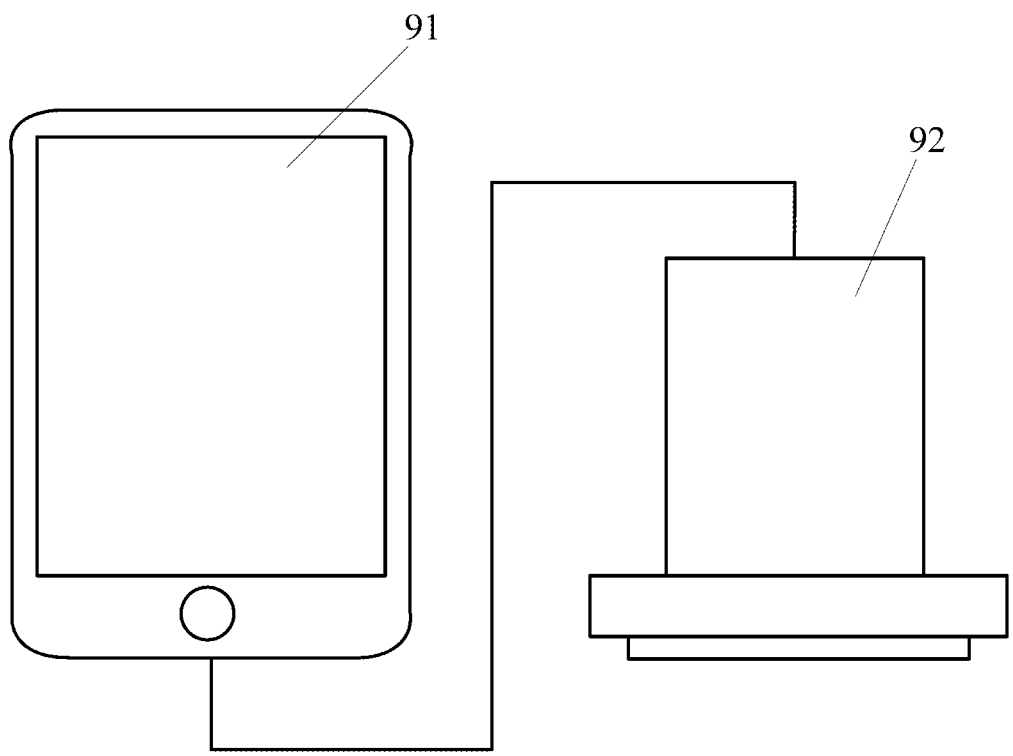
FIG. 9 is a schematic structural diagram of an ultrasonic detection system in accordance with a ninth embodiment of the present disclosure.

As shown in FIG. 9, a ninth embodiment of the present disclosure relates to an ultrasonic detection system including an ultrasonic detector 91 in the foregoing third embodiment or fourth embodiment and an ultrasonic imager 92 in the seventh embodiment.

In particular, the ultrasonic detection system may be an ultrasonic apparatus applied to human body detection, or may be an ultrasonic apparatus applied to ultrasonic flaw detection of an element. Specific application is not limited herein.

Those skilled in the art may understand that all or some of the steps of the method in accordance with the aforementioned embodiments may be implemented by a program instructing relevant hardware. The program is stored in a storage medium, and contains several instructions used to instruct a device (which may be a single-chip microcomputer, a chip, or the like) or a processor to perform all or some steps of the methods in the embodiments of the present disclosure. The foregoing storage medium may be any medium that may store a program code, such as a USB flash drive, a removable hard disk, a read-only memory (ROM), a random-access memory (RAM), a magnetic disk, or an optical disc.

Those skilled in the art should appreciate that the aforementioned embodiments are specific embodiments for implementing the present disclosure. In practice, however, many changes can be made in the forms and details of the specific embodiments without departing from the spirit and scope of the present disclosure.

What is claimed is:

1. An ultrasonic detector, comprising:
   a detection surface;
   a print head disposed at the detection surface; and
   a receiving device configured to receive information of a mark, the mark being input by an operator on an ultrasonic image;
   wherein, the print head is configured to add a mark on a surface of a detected object that contacts the detection surface, according to pixel position information of the mark on the ultrasonic image.

2. The ultrasonic detector according to claim 1, wherein the ultrasonic detector further comprises a pressure sensor and a processor, the pressure sensor disposed at the detection surface;
   the pressure sensor is configured to acquire a pressure value between the detection surface and the detected object and transmit the pressure value to the processor; and
   the processor is configured to control, in accordance with an acquired pressure value, the print head to add the mark on the surface of the detected object.

3. The ultrasonic detector according to claim 2, wherein the print head comprises a nozzle and an ink chamber, the ink chamber is filled with ink, the ink chamber is connected with the nozzle, and the nozzle is disposed at the detection surface; and
   the processor is specifically configured to control, in accordance with the pressure value, the ink in the ink chamber to be ejected from the nozzle.

4. The ultrasonic detector according to claim 2, wherein the print head comprises at least two print units.

5. The ultrasonic detector according to claim 3, wherein the print head comprises at least two print units.

6. The ultrasonic detector according to claim 4, wherein the at least two print units are evenly distributed at the detection surface.

7. The ultrasonic detector according to claim 5, wherein the at least two print units are evenly distributed at the detection surface.

8. The ultrasonic detector according to claim 2, wherein the processor is specifically configured to:
   determine a pattern of the mark and adding position information, and
   control, in accordance with the acquired pressure value, the print head to add the mark on the surface of the detected object in accordance with the pattern of the mark and the adding position information.

9. The ultrasonic detector according to claim 3, wherein the processor is specifically configured to:
   determine a pattern of the mark and adding position information, and control, in accordance with the acquired pressure value, the print head to add the mark on the surface of the detected object in accordance with the pattern of the mark and the adding position information.

10. The ultrasonic detector according to claim 1, wherein the information of the mark comprises a pattern of the mark and a display position of the mark on the ultrasonic image.

11. The ultrasonic detector according to claim 1, wherein the information of the mark indicates at least one of: a direction of a blood vessel on the ultrasonic image, and a position of the blood vessel on the ultrasonic image.

12. The ultrasonic detector according to claim 1, wherein the information of the mark indicates a position with a flaw on the ultrasonic image.

13. An ultrasonic detection method, applied to an ultrasonic imager, wherein the ultrasonic detection method comprises:
    acquiring a reflected ultrasonic signal transmitted by an ultrasonic detector;
    generating an ultrasonic image in accordance with the reflected ultrasonic signal and displaying the ultrasonic image;
    acquiring information of a mark input by an operator based on the ultrasonic image; the mark being on the ultrasonic image, and the information of the mark including a pattern of the mark and a display position of the mark on the ultrasonic image;
    determining print information in accordance with the information of the mark; and
    transmitting the print information to the ultrasonic detector, for the ultrasonic detector to add the mark on a surface of a detected object in accordance with the print information;
    wherein the determining print information in accordance with the information of the mark comprises any one of:
    (i) determining a pixel position of the mark on the ultrasonic image in accordance with the pattern of the mark and the display position of the mark;
    determining a position of a print head corresponding to the pixel position of the mark on the ultrasonic image in accordance with a corresponding relation between the pixel position of the ultrasonic image and the position of the print head; and
    causing the determined position of the print head to be taken as the print information;
    (ii) determining a pixel position of the mark on the ultrasonic image in accordance with the pattern of the mark and the display position of the mark; and
    causing the pixel position of the mark on the ultrasonic image to be taken as the print information.

14. The ultrasonic detection method according to claim 13, wherein the information of the mark indicates at least one of: a direction of a blood vessel on the ultrasonic image, and a position of the blood vessel on the ultrasonic image.

15. The ultrasonic detection method according to claim 13, wherein the information of the mark indicates a position with a flaw on the ultrasonic image.

16. An ultrasonic imager, comprising:
    at least one processor; and
    a memory in communication with the at least one processor;
    wherein the memory stores an instruction executable by the at least one processor, when the instruction is executed by the at least one processor, causing the at least one processor to perform a ultrasonic detection method comprising:
    acquiring a reflected ultrasonic signal transmitted by an ultrasonic detector;
    generating an ultrasonic image in accordance with the reflected ultrasonic signal and displaying the ultrasonic image;
    acquiring information of a mark input by an operator based on the ultrasonic image; the mark being on the ultrasonic image, and the information of the mark including a pattern of the mark and a display position of the mark on the ultrasonic image;
    determining print information in accordance with the information of the mark; and
    transmitting the print information to the ultrasonic detector, for the ultrasonic detector to add the mark on a surface of a detected object in accordance with the print information;
    wherein the determining print information in accordance with the information of the mark comprises any one of:
    (i) determining a pixel position of the mark on the ultrasonic image in accordance with the pattern of the mark and the display position of the mark;
    determining a position of a print head corresponding to the pixel position of the mark on the ultrasonic image in accordance with a corresponding relation between the pixel position of the ultrasonic image and the position of the print head; and
    causing the determined position of the print head to be taken as the print information;
    (ii) determining a pixel position of the mark on the ultrasonic image in accordance with the pattern of the mark and the display position of the mark; and
    causing the pixel position of the mark on the ultrasonic image to be taken as the print information.

17. The ultrasonic imager according to claim 16, further comprises a display screen configured to:
    display the ultrasonic image; and
    display the mark on the ultrasonic image;
    wherein the display screen is a touch screen, and the mark on the ultrasonic image is input by the operator by using a finger or a stylus.

18. The ultrasonic imager according to claim 16, further comprises a display screen configured to:
    display the ultrasonic image; and
    display the mark on the ultrasonic image;
    wherein the mark on the ultrasonic image is input by the operator by using a mouse or a keyboard.

* * * * *

UNITED STATES PATENT AND TRADEMARK OFFICE
CERTIFICATE OF CORRECTION

PATENT NO. : 11,241,891 B2
APPLICATION NO. : 16/569829
DATED : February 8, 2022
INVENTOR(S) : Luo et al.

Page 1 of 1

It is certified that error appears in the above-identified patent and that said Letters Patent is hereby corrected as shown below:

In the Claims

Column 12, Lines 21-22: Claim 1, Delete "an ultrasonic image;" and insert -- a displayed ultrasonic image representative of a detected object; --

Column 12, Line 24: Claim 1, Delete "surface of a detected" and insert -- surface of the detected --

Signed and Sealed this
Twenty-second Day of March, 2022

Drew Hirshfeld
*Performing the Functions and Duties of the
Under Secretary of Commerce for Intellectual Property and
Director of the United States Patent and Trademark Office*